United States Patent
Goya

(10) Patent No.: US 8,210,061 B2
(45) Date of Patent: Jul. 3, 2012

(54) GAS SENSOR FITTING STRUCTURE

(75) Inventor: Yoichiro Goya, Susono (JP)

(73) Assignee: Toyota Jidosha Kabushiki Kaisha, Toyota-shi (JP)

( * ) Notice: Subject to any disclaimer, the term of this patent is extended or adjusted under 35 U.S.C. 154(b) by 402 days.

(21) Appl. No.: 12/447,665

(22) PCT Filed: Sep. 25, 2008

(86) PCT No.: PCT/IB2008/002495
§ 371 (c)(1),
(2), (4) Date: Apr. 29, 2009

(87) PCT Pub. No.: WO2009/040641
PCT Pub. Date: Apr. 2, 2009

(65) Prior Publication Data
US 2010/0064663 A1    Mar. 18, 2010

(30) Foreign Application Priority Data
Sep. 27, 2007    (JP) .................. 2007-251741

(51) Int. Cl.
*G01D 21/00*    (2006.01)
(52) U.S. Cl. ..................................... 73/866.5
(58) Field of Classification Search ................. 73/23.31, 73/1.06, 866.5; 204/424
See application file for complete search history.

(56) References Cited

U.S. PATENT DOCUMENTS

| | | | |
|---|---|---|---|
| 7,901,556 B2 * | 3/2011 | Yamada | 204/428 |
| 2005/0016849 A1 | 1/2005 | Ikoma et al. | |
| 2005/0241937 A1 | 11/2005 | Shichida et al. | |
| 2006/0108222 A1 * | 5/2006 | Yamada et al. | 204/431 |
| 2007/0240485 A1 * | 10/2007 | Kanao | 73/1.06 |
| 2008/0236248 A1 | 10/2008 | Ikoma et al. | |
| 2010/0000290 A1 * | 1/2010 | Goya | 73/23.31 |

FOREIGN PATENT DOCUMENTS

| | | |
|---|---|---|
| EP | 1 471 346 | 10/2004 |
| EP | 1 541 999 | 6/2005 |
| JP | 61-147344 U | 9/1986 |
| JP | 02-148464 U | 12/1990 |
| JP | 10 148623 | 6/1998 |
| JP | 2000-105215 A | 4/2000 |
| JP | 2000-171429 A | 6/2000 |
| JP | 2004 93337 | 3/2004 |
| JP | 2007-198306 A | 8/2007 |
| JP | 2007-211607 A | 8/2007 |

OTHER PUBLICATIONS

Japanese Office Action issued on Feb. 7, 2012, in JP Patent Application No. 2007-251741 (with partial English-language translation).

* cited by examiner

Primary Examiner — Jewel V Thompson

(74) Attorney, Agent, or Firm — Oblon, Spivak, McClelland, Maier & Neustadt, L.L.P.

(57) ABSTRACT

A gas sensor is fitted to an exhaust pipe such that an end face in which a vent-hole is formed is not visible from any position of inlet portions of the exhaust pipe. Thus, it is possible to suppress entry of condensed water through the vent hole formed in the end face of the gas sensor. As a result, it is possible to minimize occurrence of a crack in the gas sensor.

16 Claims, 10 Drawing Sheets

GAS SENSOR FITTING STRUCTURE

BACKGROUND OF THE INVENTION

1. Field of the Invention

The invention relates to a gas sensor fitting structure.

2. Description of the Related Art

In an internal combustion engine, gas sensors such as an air-fuel ratio sensor and an oxygen sensor are fitted to an exhaust pipe. Such gas sensor usually includes a sensor element, a heater that activates the sensor element, and a cover that covers the sensor element. A vent-hole is formed in the cover so that the sensor element is exposed to the exhaust gas that flows into the gas sensor through the vent-hole.

Japanese Patent Application Publication No. 10-148623 (JP-A-10-148623) describes a fluid sensor fitting structure. More specifically, JP-A-10-148623 describes a structure in which a fluid sensor is fitted to a fluid pipe with the central axis of the fluid sensor inclined with respect to the direction that is perpendicular to the direction in which the fluid flows. This fitting structure reduces the possibility that foreign matter contained in the fluid in the cover will adhere to a sensor element.

During start-up of an internal combustion engine, the water that has been condensed from the exhaust gas may remain in an exhaust pipe after the immediately preceding engine stop, or water may be condensed from the exhaust gas that is discharged from the internal combustion engine after the engine start if the exhaust gas contacts an inner wall of the exhaust pipe that is at a low temperature. If the condensed water contacts a sensor element while the sensor element is heated by a heater, a crack may occur in the sensor element. The condensed water generated in the exhaust pipe disperses in various directions as the exhaust gas flows. Therefore, even if the fitting structure described in JP-A-10-148623 is applied to, for example, the above-described air-fuel ratio sensor, there is still a possibility that the condensed water will contact the sensor element.

SUMMARY OF THE INVENTION

The invention provides a gas sensor fitting structure which makes it possible to suppress entry of condensed water into a cover and to minimize occurrence of a crack in a sensor element due to contact of the condensed water with the sensor element.

A first aspect of the invention relates to a gas sensor fitting structure for fitting a gas sensor to an exhaust pipe of an internal combustion engine, and the gas sensor includes a sensor element and a cover which covers the sensor element, and has a vent-hole at an end portion of the cover. The exhaust pipe has multiple inlet portions, and the gas sensor is fitted to the exhaust pipe at a predetermined fitting angle so that the end portion is not visible from any position of the multiple inlet portions. With this fitting structure, it is possible to suppress entry of the condensed water into the cover through the vent-hole formed in the end portion of the cover. Thus, it is possible to minimize occurrence of a crack in the sensor element due to contact of the condensed water with the sensor element.

A second aspect of the invention relates to a gas sensor fitting structure for fitting a gas sensor to an exhaust pipe of an internal combustion engine, and the gas sensor includes a sensor element and a cover which covers the sensor element, and has a vent-hole at an end portion of the cover. The exhaust pipe has a bent portion, and the gas sensor is fitted to the exhaust pipe at a predetermined fitting angle so that the end portion is not visible via the bent portion from any position of an inlet portion of the exhaust pipe. With this fitting structure as well, it is possible to suppress entry of the condensed water into the cover through the vent-hole formed in the end portion of the cover.

In the gas sensor fitting structure according to the first aspect of the invention, the exhaust pipe may have a bent portion, and the gas sensor may be fitted to the exhaust pipe at the predetermined fitting angle so that the end portion is not visible via the bent portion from any position of the inlet portions of the exhaust pipe.

The gas sensor may be fitted to the exhaust pipe at the predetermined fitting angle so that the end portion is not visible from any position on a virtual plane that is surrounded by the inlet portion.

The virtual plane may include an end face of the inlet portion of the exhaust pipe The predetermined fitting angle θ satisfies the following formula; $\theta \leqq 90° - \arctan\{(h-t)/l\}$ where h is a diameter of the exhaust pipe, t is a distance from an inner wall face of the exhaust pipe to the end portion, and l is a distance from the inlet portion of the exhaust pipe to the gas sensor.

The distance from the inlet portion of the exhaust pipe to the gas sensor may be a length of a line segment in parallel with an axis of the exhaust pipe while extending from the inlet portion of the exhaust pipe to the end portion, and the predetermined fitting angle of the gas sensor with respect to the exhaust pipe may be the angle between the axis of the exhaust pipe and the axis of the gas sensor.

The inlet portion of the exhaust pipe may be connected to an exhaust port of the internal combustion engine, and the predetermined fitting angle of the gas sensor with respect to the exhaust pipe may be decreased as the distance between the inlet portion and the gas sensor decreases.

The gas sensor may be an air-fuel ratio sensor that linearly detects an air-fuel ratio based on an oxygen concentration in exhaust gas that is discharged from the internal combustion engine.

BRIEF DESCRIPTION OF THE DRAWINGS

The foregoing and further features and advantages of the invention will become apparent from the following description of example embodiments with reference to the accompanying drawings, wherein the same or corresponding portions will be denoted by the same reference numerals and wherein.

DETAILED DESCRIPTION OF THE EXAMPLE EMBODIMENTS

Hereafter, a first embodiment of the invention will be described with reference to the accompanying drawings.

Figure 1:
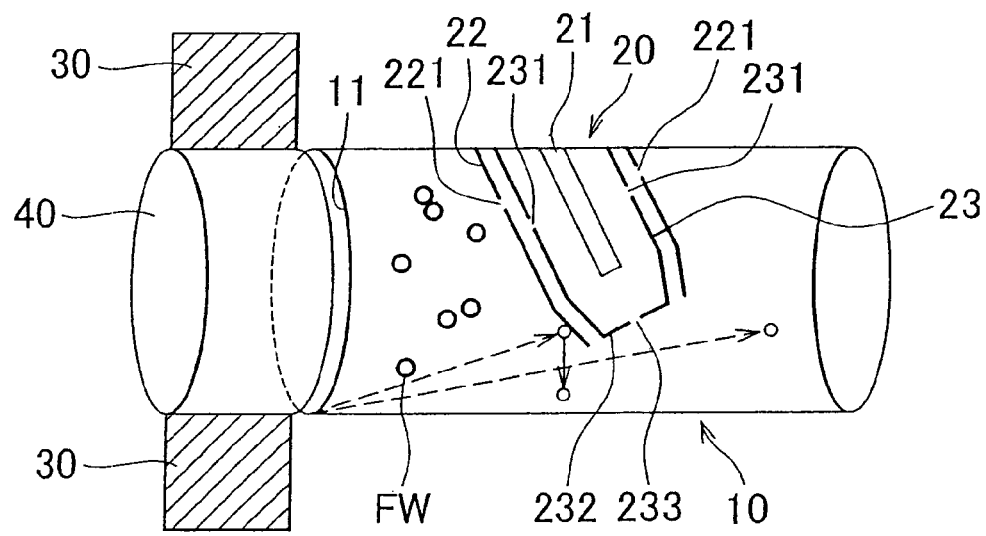
FIG. 1 shows a gas sensor fitting structure according to a first embodiment of the invention.

FIG. 1 is a view showing a gas sensor fitting structure according to the first embodiment of the invention. A gas sensor 20 according to the first embodiment of the invention is an air-fuel ratio sensor that linearly detects an air-fuel ratio based on an oxygen concentration in the exhaust gas. However, the gas sensor 20 is not limited to such air-fuel ratio sensor. The gas sensor 20 may be an oxygen sensor that determines whether an air-fuel ratio is richer or leaner than the stoichiometric air-fuel ratio based on an oxygen concentration in the exhaust gas or various gas sensors that detect, for example, a NOx concentration, a CO concentration, and a HC concentration. The gas sensor 20 includes a stacked sensor element 21. Alternatively, the gas sensor 20 may include a cup-shaped sensor element.

The gas sensor 20 is fitted to an exhaust pipe 10 in such a manner that a portion of the gas sensor 20 projects into the space within the exhaust pipe 10. As shown in FIG. 1, the gas sensor 20 is fitted to the exhaust pipe 10 in such a manner that the gas sensor 20 is inclined with respect to the exhaust pipe 10. An inlet portion 11 of the exhaust pipe 10 is connected to an exhaust port 40 of an internal combustion engine. The inlet portion 11 is formed in an annular shape. The gas sensor 20 is fitted to the exhaust pipe 10 that linearly extends from the inlet portion 11. In FIG. 1, the inlet portion 11 and the exhaust port 40 are shown in a separated manner in order to clearly indicate the inlet portion 11 of the exhaust pipe 10. The exhaust port 40 is formed in a cylinder head 30 of the internal combustion engine. The exhaust gas discharged from the exhaust port 40 is introduced into the exhaust pipe 10 and discharged to the outside of the internal combustion engine after toxic components are removed by an exhaust gas catalyst (not shown) that is arranged in a downstream portion of the exhaust pipe 10.

A cover that covers the sensor element 21 of the gas sensor 20 has a double structure formed of an outer cover 22 and an inner cover 23. The inner cover 23 is formed in a cylindrical shape, and has a circular end face (end portion) 232. The outer cover 22 is also formed in a cylindrical shape, but does not have an end face. The outer cover 22 is formed in such a manner that the end face 232 of the inner cover 23 is exposed to the exhaust gas in the exhaust pipe 10.

Vent-holes 221 are formed in a side face of the outer cover 22, and vent-holes 231 are formed in a side face of the inner cover 23. A vent-hole 233 is formed in the end face 232 of the inner cover 23. The exhaust gas flows into the inside of the outer cover 22 through the vent-holes 221, flows into the inside of the inner cover 23 through the vent-holes 231, contacts the sensor element 21, and is discharged to the outside of the gas sensor 20.

A heater (not shown) that increases the temperature of the sensor element 21 to an activation temperature is embedded in the sensor element 21. The operation of the heater is controlled by an electronic control unit (not shown).

Figure 2:
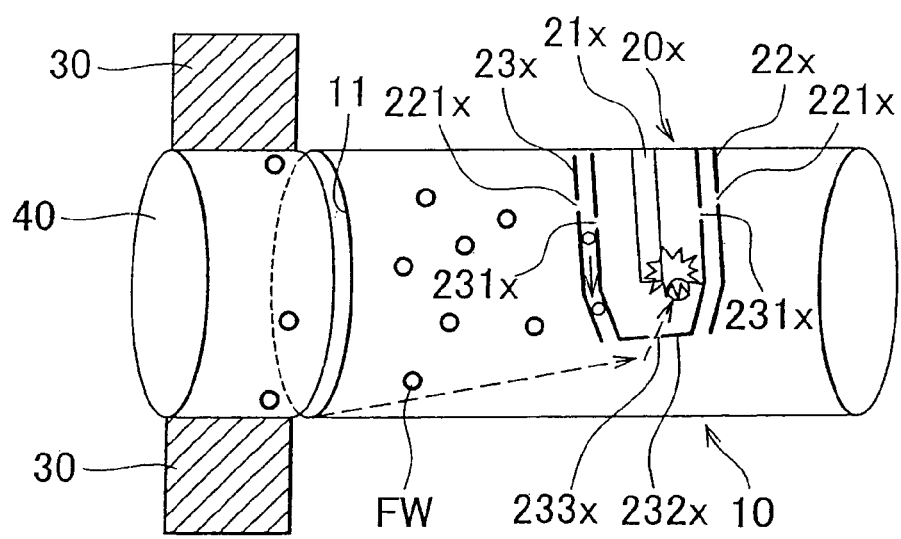
FIG. 2 shows a gas sensor fitting structure according to related art.

Next, inconveniences caused by a gas sensor fitting structure according to related art will be described. FIG. 2 shows the gas sensor fitting structure according to the related art. Portions in FIG. 2 that are the same as those in FIG. 1 are denoted by the same reference numerals as those in FIG. 1, and description thereof will not be provided below. As shown in FIG. 2, in a fitting structure for fitting a gas sensor 20x to the exhaust pipe 10 according to the related art, the gas sensor 20x is fitted to the exhaust pipe 10 in such a manner that the gas sensor 20x is slightly inclined with respect to the exhaust pipe 10. Therefore, condensed water FW that is generated in the exhaust pipe 10 may reach a sensor element 21x through a vent-hole 233x.

However, in the gas sensor fitting structure according to the first embodiment of the invention shown in FIG. 1, the gas sensor 20 is fitted to the exhaust pipe 10 in such a manner that the gas sensor 20 is inclined with respect to the exhaust pipe 10 by an amount larger than that in the gas sensor fitting structure according to the related art. Therefore, although there is a possibility that the condensed water FW will adhere to an end portion of the outer cover 22, it is possible to minimize the possibility that the condensed water FW will enter the inside of the inner cover 23 through the vent-hole 233. Accordingly, it is possible to minimize occurrence of a crack in the sensor element 21 due to the condensed water FW.

Figure 3A:
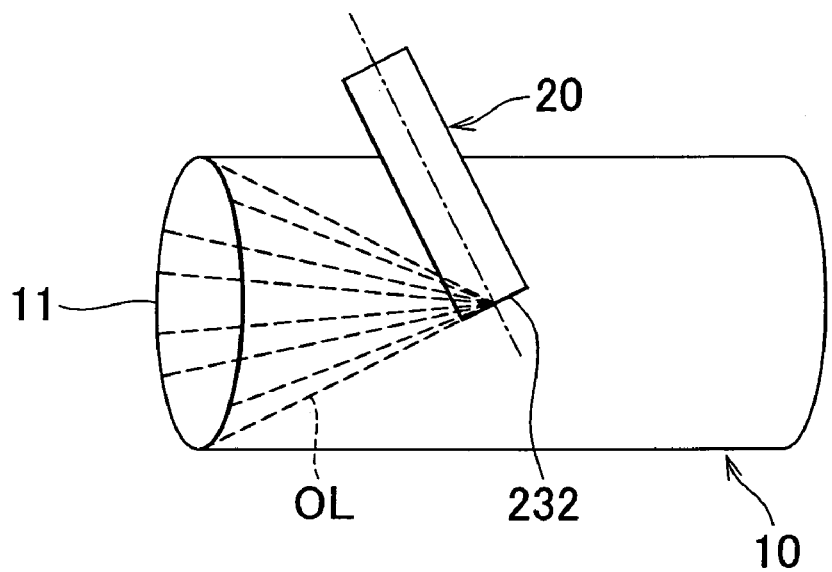
FIGS. 3A and 3B are views for comparing the gas sensor fitting structure according to the first embodiment of the invention with the gas sensor fitting structure according to the related art.
Figure 3B:
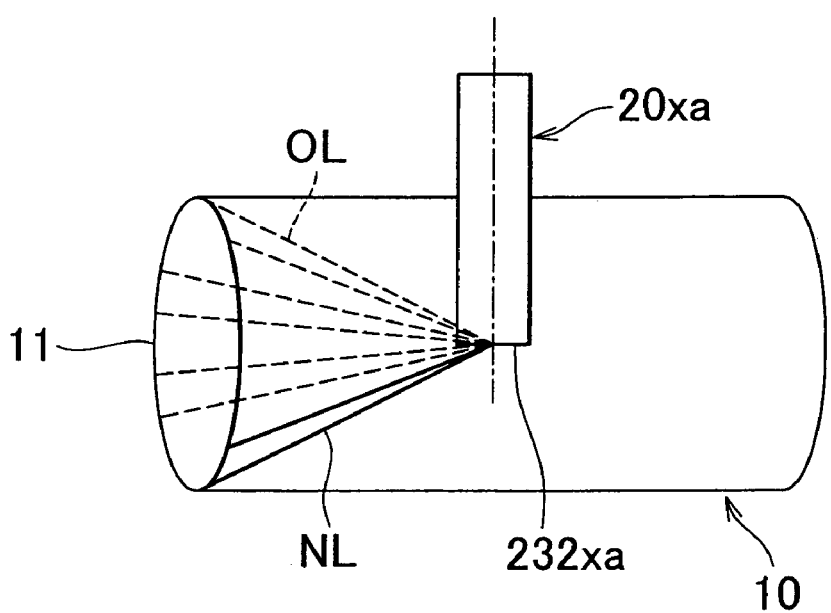

Next, the effects of the gas sensor fitting structure according to the first embodiment of the invention will be described. FIGS. 3A and 3B are views for comparing the gas sensor fitting structure according to the first embodiment of the invention with the gas sensor fitting structure according to related art. FIG. 3A shows the gas sensor fitting structure according to the first embodiment of the invention, and FIG. 3B shows the gas sensor fitting structure according to the related art. FIGS. 3A and 3B schematically show the structure of the gas sensor 20 and the structure of a gas sensor 20xa, respectively, to facilitate the explanation. FIG. 3B shows a case in which the gas sensor 20xa is fitted to the exhaust pipe 10 in such a manner that the axis of the gas sensor 20xa extends perpendicularly to the axis of the exhaust pipe 10.

As shown in FIG. 3A, the gas sensor 20 is fitted to the exhaust pipe 10 in such a manner that the gas sensor 20 is inclined largely with respect to the exhaust pipe 10. As a result, the end face 232 of the gas sensor 20 is not visible from the inlet portion 11. More specifically, the gas sensor 20 is fitted to the exhaust pipe 10 at a predetermined fitting angle so that the end face 232 is not visible from any position on a virtual plane that includes the end face of the inlet portion 11 and that is surrounded by the inlet portion 11.

In FIG. 3A, directions in which line segments from points on the edge of the inlet portion 11 to the center of the end face 232 extend are referred to as eye directions OL. As shown in FIG. 3A, the center of the end face 232 is not visible from any of the eye directions OL. Therefore, the vent-hole 233 formed in the end face 232 is not visible from the inlet portion 11. Accordingly, it is possible to minimize occurrence of the situation in which the condensed water that adheres to an inner peripheral wall face of the inlet portion 11 or an inner peripheral wall face of the exhaust port 40 will disperse due to a flow of the exhaust gas and enter the vent-hole 233 formed in the end face 232. Thus, it is possible to minimize occurrence of a crack in the sensor element 21 due to the condensed water.

In contrast, according to the related art shown in FIG. 3B, the gas sensor 20xa is fitted to the exhaust pipe 10 in such a manner that the axis of the gas sensor 20xa extends perpendicularly to the axis of the exhaust pipe 10. Therefore, when the gas sensor 20xa is fitted to the exhaust pipe 10, an end face 232xa is visible from a part of the inlet portion 11. In FIG. 3B, directions in which line segments from points on the upper-side portion of the edge of the inlet portion 11 to the center of the end face 232xa extend are referred to as eye directions OL (indicated by dashed lines), and directions in which line segments from points on the lower-side portion of the edge of the inlet portion 11 to the center of the end face 232xa extend are referred to as eye directions NL (indicated by solid lines). As shown in FIG. 3B, the center of the end face 232xa is not visible from the eye directions OL but visible from the eye directions NL.

Therefore, there is only a low possibility that the condensed water, which adheres to portions near the viewpoints from which the line segments extend in the eye directions OL, will adhere to the end face 232xa, but there is a high possibility that the condensed water, which adheres to portions near the viewpoints from which the line segments extend in the eye directions NL, will disperse due to a flow of the exhaust gas and adhere to the end face 232xa. If the condensed water adheres to the end face 232xa, the condensed water may enter the inside of an inner cover 23x through the vent-hole 233x formed in the end face 232xa and reach the sensor element 21x.

However, according to the first embodiment of the invention shown in FIG. 3A, it is possible to minimize the possibility that the condensed water will contact the sensor element 21. This is because, as shown in FIG. 3A, the gas sensor 20 is fitted to the exhaust pipe 10 in such a manner that the gas sensor 20 is inclined with respect to the exhaust pipe 10. Therefore, the end face 232 is not visible from the inlet portion 11.

Figure 4:
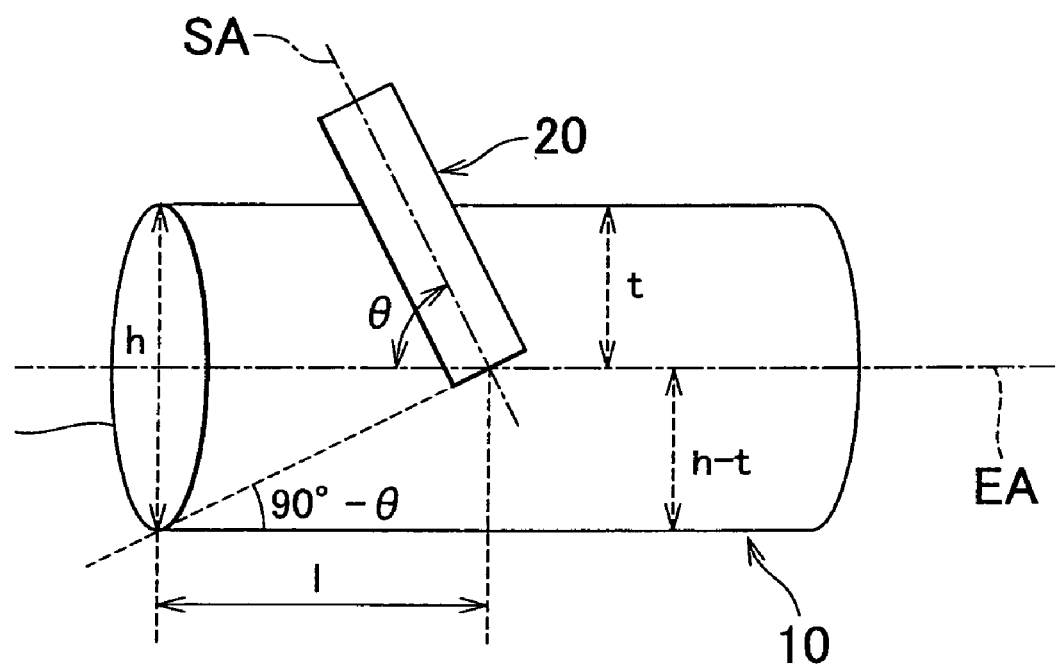
FIG. 4 shows an angle at which the gas sensor is fitted to an exhaust pipe according to the first embodiment of the invention.

Next, an angle at which the gas sensor 20 is fitted to the exhaust pipe 10 (hereinafter, referred to as "fitting angle of the gas sensor 20" where appropriate) according to the first embodiment of the invention will be described. FIG. 4 is a view illustrating the fitting angle of the gas sensor 20 according to the first embodiment of the invention. A case in which the gas sensor 20 is fitted to a linearly formed portion of the exhaust pipe 10 will be described below.

A reference character "h" denotes the diameter of the exhaust pipe 10. A reference character "t" denotes the distance from the inner wall face of the exhaust pipe 10 to the end face 232 of the gas sensor 20. More specifically, the reference character "t" denotes the distance from the inner wall face of the exhaust pipe 10 to the center of the end face 232. A reference character "l" denotes the distance from the inlet portion 11 to the gas sensor 20. More specifically, the reference character "l" denotes the length of the line that extends in parallel with an axis EA of the exhaust pipe 10 and that extends from the inlet portion 11 to the center of the end face 232. A reference character "θ" denotes an inclination angle (fitting angle) at which the gas sensor 20 is fitted to the exhaust pipe 10. More specifically, the reference character "θ" denotes an angle between the axis EA of the exhaust pipe 10 and an axis SA of the gas sensor 20. As shown in FIG. 4, if the line, which extends in the eye direction when the end face 232 is visible from the viewpoint that lies in the lower end portion of the inlet portion 11, is in parallel with the end face 232, Equation 1 is satisfied.

$$\tan(90°-\theta)=(h-t)/1 \qquad \text{Equation 1}$$

Equation 1 may be modified into Equation 2.

$$\theta=90°-\arctan\{(h-t)/1\} \qquad \text{Equation 2}$$

Accordingly, when the inclination angle θ of the gas sensor 20 satisfies Equation 3, the end face 232 is not visible from the inlet portion 11.

$$\theta \leq 90°-\arctan\{(h-t)/1\} \qquad \text{Equation 3}$$

Figure 5A:
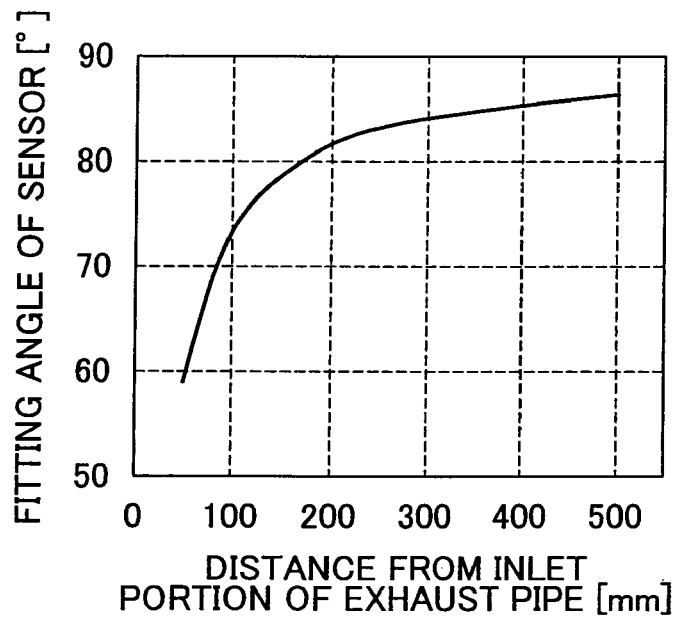
FIGS. 5A and 5B show the relationship between a position at which the gas sensor is fitted to the exhaust pipe and an angle at which the gas sensor is fitted to the exhaust pipe according to the first embodiment of the invention.
Figure 5B:
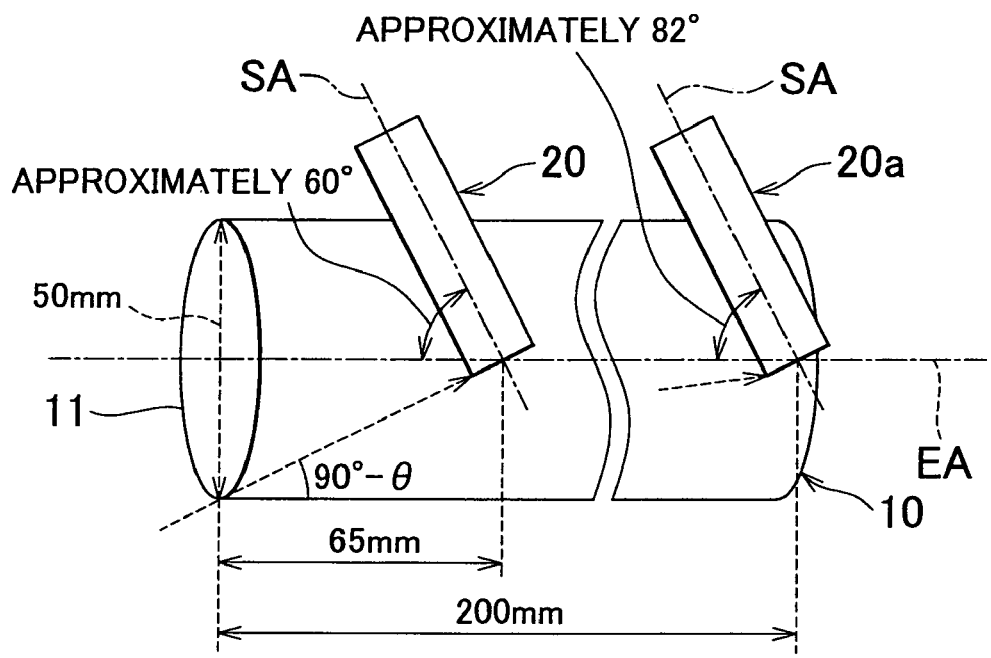

Next, a concrete example of the relationship between a position at which the gas sensor 20 is fitted to the exhaust pipe 10 (hereinafter; referred to as "fitting position of the gas sensor 20" where appropriate) and an angle at which the gas sensor 20 is fitted to the exhaust pipe 10 (hereinafter, referred to as "fitting angle of the gas sensor 20" where appropriate) according to the first embodiment of the invention will be described with reference to FIGS. 5A and 5B. FIG. 5A is a map that shows the relationship between the distance from the inlet portion 11 of the exhaust pipe 10 to the gas sensor 20 and the fitting angle of the gas sensor 20.

When a fitting angle of the gas sensor 20 is equal to or smaller than the fitting angle indicated by the line in FIG. 5A, the end face 232 is not visible from the inlet portion 11. As the distance from the inlet portion 11 to the gas sensor 20 decreases, the fitting angle of the gas sensor 20 needs to be decreased. That is, as the distance from the inlet portion 11 to the gas sensor 20 decreases, the gas sensor 20 needs to be fitted to the exhaust pipe 10 at a smaller fitting angle. FIG. 5B shows the fitting angle when the distance from the inlet portion 11 to the fitting position of the gas sensor 20 is 65 millimeters, and the fitting angle when the distance from the inlet portion 11 to the fitting position of the gas sensor 20 is 200 millimeters. When the distance from the inlet portion 11 to the fitting position of the gas sensor 20 is 65 millimeters, the fitting angle of the gas sensor 20 needs to be equal to or smaller than approximately 65 degrees with respect to the axis EA of the exhaust pipe 10. When the distance is 200 millimeters, the fitting angle needs to be equal to or smaller than approximately 82 degrees with respect to the axis EA of the exhaust pipe 10.

It is possible to set the fitting position of the gas sensor 20 to a position near the inlet portion 11 while minimizing the possibility of a contact of the condensed water with the sensor element 21 by changing the fitting angle of the gas sensor 20 based on the fitting position of the gas sensor 20 as described above. It is possible to expose the gas sensor 20 to the exhaust gas having a higher temperature by fitting the gas sensor 20 to a portion closer to the inlet portion 11. Thus, for example, when the internal combustion engine is started while it is cold, the sensor element 21 of the gas sensor 20 is activated more promptly. When the gas sensor fitting structure according to the first embodiment of the invention is applied to a multi-cylinder internal combustion engine, a gas sensor should be fitted to an exhaust pipe in such a manner that Equation 3 is satisfied on all multiple inlet portions of the exhaust pipe. In this way, it is possible to minimize the possibility that the condensed water will contact a sensor element.

Figure 6A:
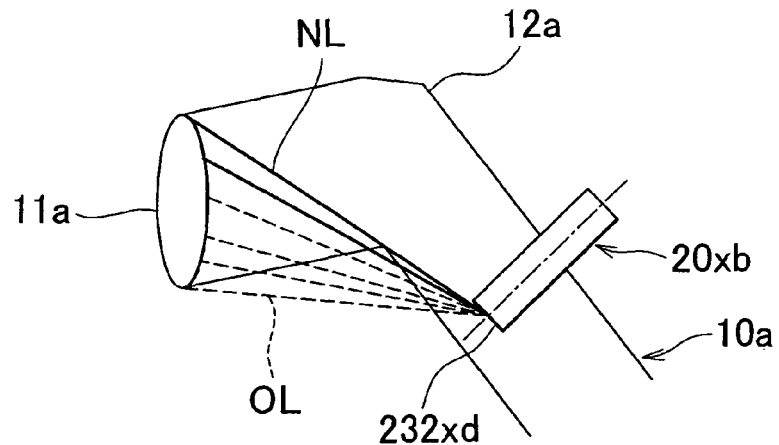
FIGS. 6A to 6C each show a gas sensor fitting structure for fitting a gas sensor to an exhaust pipe that has a bent portion according to a second embodiment of the invention.
Figure 6B:
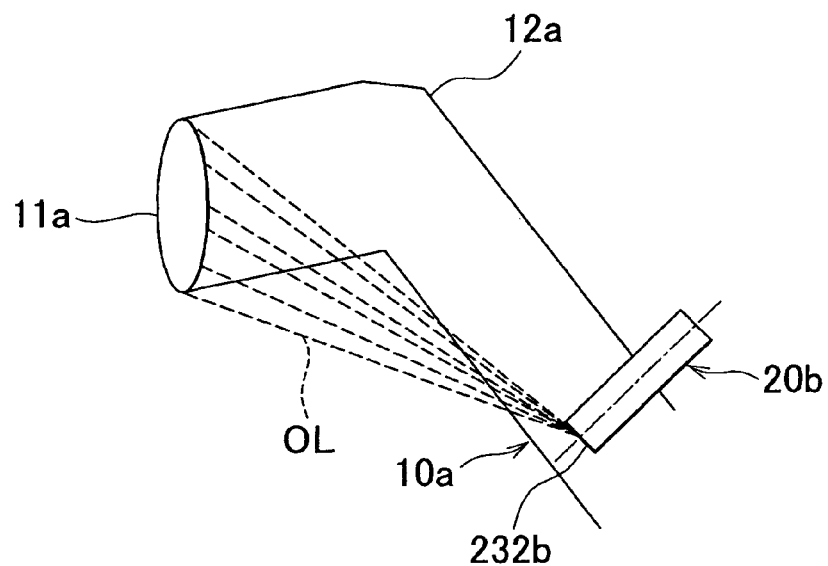
Figure 6C:
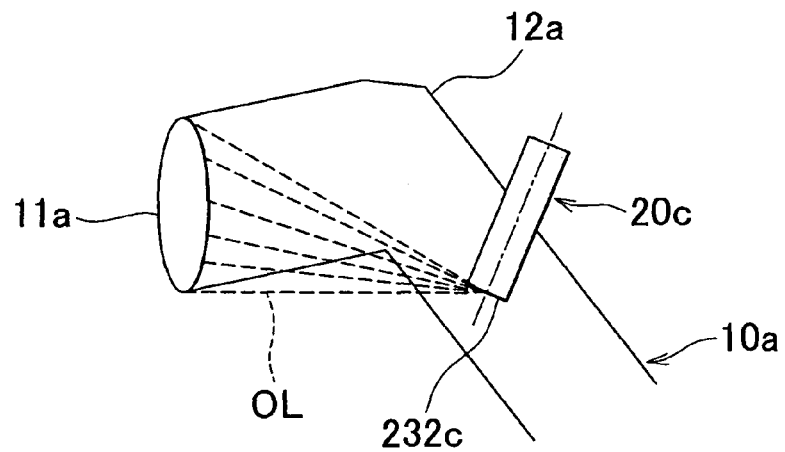

Next, a gas sensor fitting structure according to a second embodiment of the invention will be described. In the second embodiment of the invention, a gas sensor is fitted to an exhaust pipe that includes a bent portion. FIGS. 6A to 6C each show the gas sensor fitting structure for fitting the gas sensor to the exhaust pipe that includes the bent portion. FIG. 6A shows a case in which an end face of the gas sensor is visible from an inlet portion of the exhaust pipe.

As shown in FIG. 6A, a bent portion 12a is formed at a middle portion of an exhaust pipe 10a, and a gas sensor 20xb is fitted to the exhaust pipe 10a at a position downstream of the bent portion 12a. In FIG. 6A, directions in which line segments from points on the lower-side portion of the edge of an inlet portion 11a to the center of an end face 232xd extend are referred to as eye directions OL (indicated by dashed lines), and directions in which line segments from points on the upper-side portion of the edge of the inlet portion 11a to the center of the end face 232xd extend are referred to as eye directions NL (indicated by solid lines). As shown in FIG. 6A, the end face 232xd is not visible from any of the eye directions OL, because the view is blocked by the bent portion 12a. In contrast, the end face 232xd is visible from the eye directions NL, because the view is not blocked by the bent portion 12a.

As shown in FIG. 6A, when the end face 232xd is visible from a part of the inlet portion 11a despite the presence of the bent portion 12a, there is a possibility that the condensed water, which adheres to a portion near the part of the inlet portion 11a, will adhere to the end face 232xd due to a flow of the exhaust gas. Therefore, the condensed water may flow into the gas sensor through the vent-hole formed in the end face 232xd and contact a sensor element of the gas sensor 20xb.

FIG. 6B shows a case in which an end face of a gas sensor is not visible from any position of an inlet portion of the exhaust pipe. As shown in FIG. 6B, a gas sensor 20b is fitted to the exhaust pipe 10a at a position that is farther from the inlet portion 11a than the gas sensor 20xb is. In FIG. 6B, directions in which line segments from points on the edge of the inlet portion 11a to the center of an end face 232b extend are referred to as eye directions OL (indicated by dashed lines). As shown in FIG. 6B, the end face 232b is not visible from any of the eye directions OL because the view is completely blocked by the bent portion 12a.

Therefore, a vent-hole formed in the end face 232b is not visible as well. If the gas sensor 20b is fitted to the exhaust pipe 10a in such a manner that the vent-hole formed in the end face 232b is not visible due to the presence of the bent portion 12a, it is possible to suppress entry of the condensed water that adheres to a portion near the inlet portion 11a into the gas sensor 20b through the vent-hole formed in the end face 232b.

FIG. 6C shows another example of a case in which an end face of a gas sensor is not visible from any position of an inlet portion of the exhaust pipe. As shown in FIG. 6C, a gas sensor 20c is fitted to the exhaust pipe 10a at a position substantially the same as the position at which the gas sensor 20xb shown in FIG. 6A is fitted to the exhaust pipe 10a. However, the gas sensor 20c differs from the gas sensor 20xb in the fitting angle. The gas sensor 20c is fitted to the exhaust pipe 10a in such a manner that an end face 232c faces away from the plane surrounded by the inlet portion 11a by an amount larger than that in the gas sensor 20xb. The end face 232c faces away from the plane surrounded by the inlet portion 11a at a predetermined fitting angle.

In FIG. 6C, directions in which line segments from points on the edge of the inlet portion 11a to the center of the end face 232c extend are referred to as eye directions OL (indicated by dashed lines). As shown in FIG. 6C, the end face 232c is not visible from any position on the lower-side portion of the inlet portion 11a in the eye directions OL, because the view is blocked by the bent portion 12a. In addition, unlike the case of the gas sensor 20xb shown in FIG. 6A, the end face 232c is not visible from any position on the upper-side portion of the inlet portion 11a in the, eye directions OL. This is because the gas sensor 20c is fitted to the exhaust pipe 10a at the predetermined fitting angle so that the end face 232c faces away from the plane surrounded by the inlet portion 11a. If the gas sensor 20c is fitted to the exhaust pipe in this manner, it is possible to suppress entry of the condensed water that adheres to a portion near the inlet portion 11a into the gas sensor 20c through a vent-hole formed in the end face 232c.

Figure 7:
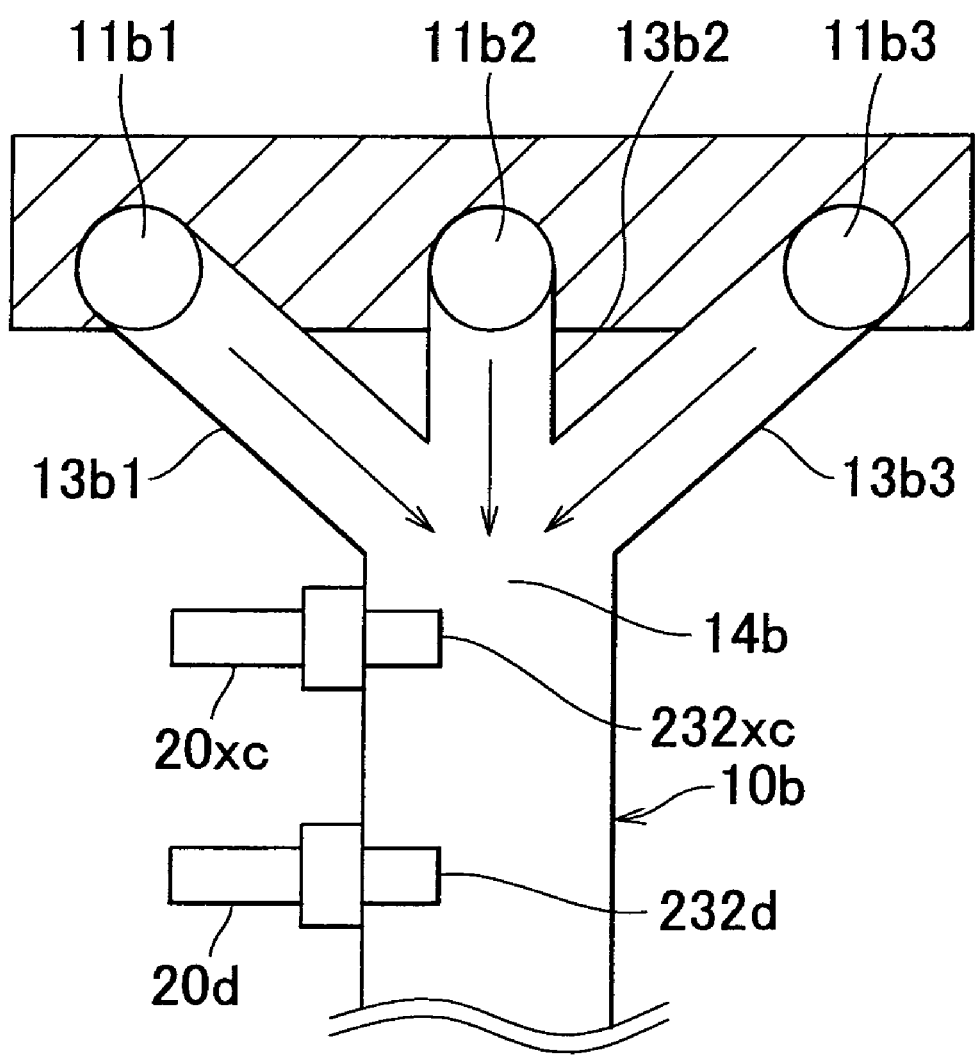
FIG. 7 shows a gas sensor fitting structure for fitting a gas sensor to an exhaust pipe of a multi-cylinder internal combustion engine according to a third embodiment of the invention.

Next, a third embodiment of the invention will be described. The third embodiment of the invention relates to a gas sensor fitting structure for fitting a gas sensor to an exhaust pipe of a multi-cylinder internal combustion engine. FIG. 7 shows a gas sensor fitting structure for fitting the gas sensor to the exhaust pipe of a multi-cylinder internal combustion engine. As shown in FIG. 7, an exhaust pipe 10b is formed in such a manner that upstream-side exhaust pipes 13b1, 13b2 and 13b3 that include inlet portions 11b1, 11b2 and 11b3, respectively, join into one exhaust pipe via a merging portion 14b. The inlet portions 11b1, 11b2, 11b3 are connected to exhaust ports of respective cylinders. As shown in FIG. 7, a gas sensor 20xc is fitted to an exhaust pipe 10b at a position near the merging portion 14b. Another gas sensor 20d is fitted to the exhaust pipe 10b at a position that is downstream of the merging portion 14b in the direction in which exhaust gas flows.

Figure 8A:
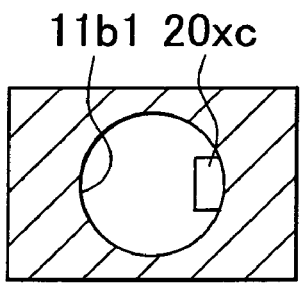
FIGS. 8A to 8C show the gas sensor being visible from multiple inlet portions of the exhaust pipes.
Figure 8B:
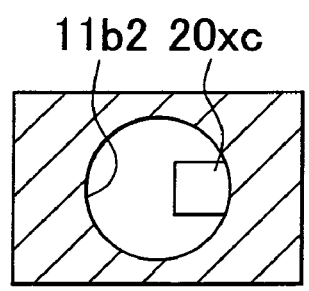
Figure 8C:
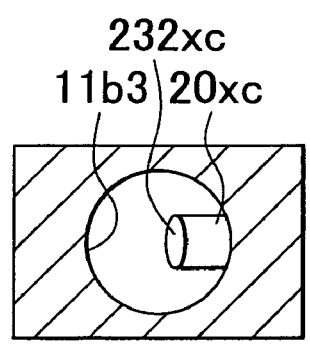

FIG. 8A to 8C show the gas sensor 20xc visible from the inlet portions 11b1, 11b2 and 11b3 of the exhaust pipes 13b1, 13b2 and 13b3, respectively. As shown in FIGS. 8A and 8B, when the gas sensor 20xc is visible from the inlet portions 11b1 and 11b2 in the downstream direction, an end face 232xc of the gas sensor 20xc is not visible. However, when the gas sensor 20xc is visible from the inlet portion 11b3 in the downstream direction, the end face 232xc is visible. This is because the direction from which the end face 232xc is visible varies among the inlet portions 11b1, 11b2 and 11b3.

Therefore, there is a possibility that the condensed water that adheres to a portion near the inlet portion 11b3 will flow through the upstream-side exhaust pipe 13b3 and enter a vent-hole that is formed in the end face 232xc. In contrast, the gas sensor 20d shown in FIG. 7 is fitted to the exhaust pipe 10b at a position downstream of the merging portion 14b so that an end face 232d is not visible from any of the inlet portions 11b1, 11b2, 11b3. Therefore, it is possible to minimize the possibility that the condensed water will contact the gas sensor 20d. As a result, it is possible to suppress occurrence of a crack in a sensor element of the gas sensor 20d due, to entry of the condensed water into the gas sensor 20d.

Figure 9A:
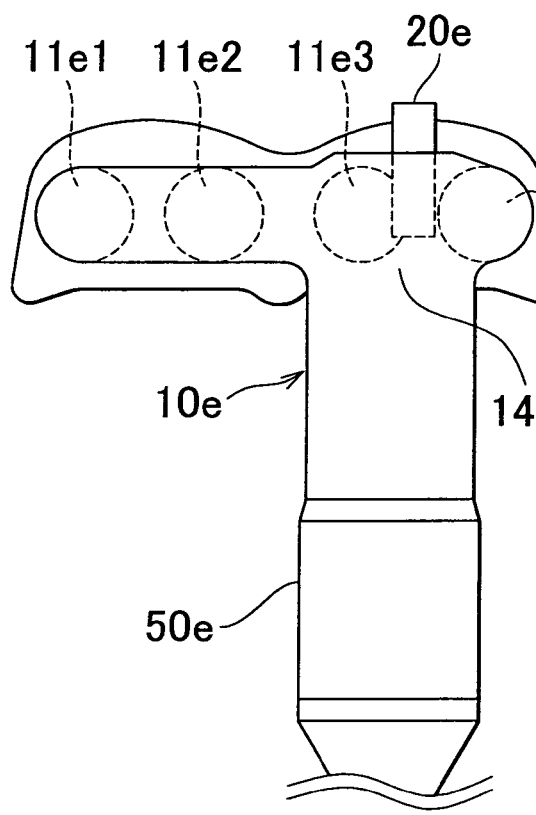
FIGS. 9A and 9B show a first example of the gas sensor fitting structure according to the third embodiment of the invention.
Figure 9B:
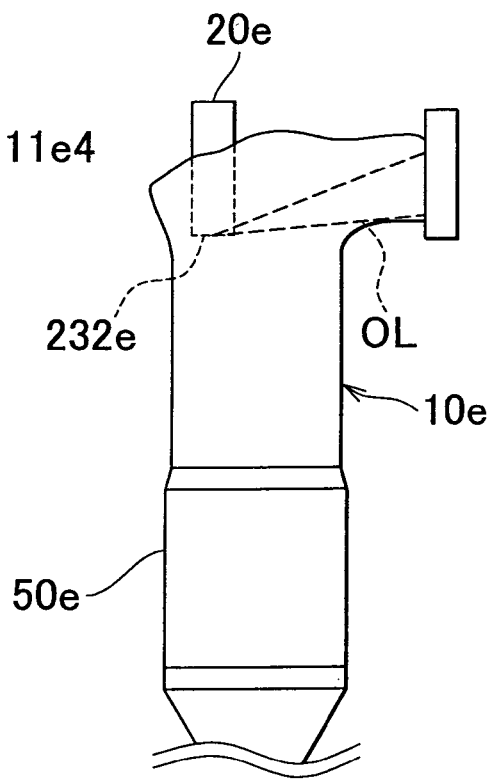

Next, concrete examples of the gas sensor fitting structure according to the third embodiment of the invention will be described briefly. FIGS. 9A and 9B show a first example of the gas sensor fitting structure according to the third embodiment of the invention. FIG. 9A is a top view of an exhaust pipe 10e, and FIG. 9B is a side view of the exhaust pipe 10e. The exhaust pipe 10e includes inlet portions 11e1 to 11e4, and a gas sensor 20e is fitted to the exhaust pipe 10e at a position near a merging portion 14e. The gas sensor 20e is fitted to the exhaust pipe 10e at a position upstream of a catalyst 50e that is arranged in the exhaust pipe 10e. As shown in FIG. 9B, the gas sensor 20e is fitted to the exhaust pipe 10e in such a manner that the gas sensor 20e itself is visible from the inlet portions 11e1 to 11e4 but an end face 232e is not visible from any of the inlet portions 11e1 to 11e4. As described above, even when the gas sensor 20e is fitted to the exhaust pipe 10e at a position near the merging portion 14e, if the end face 232e is not visible from any of the inlet portions 11e1 to 11e4, it is possible to minimize occurrence of a crack in a sensor element of the gas sensor 20e due to entry of the condensed water into the gas sensor 20e.

Figure 10A:
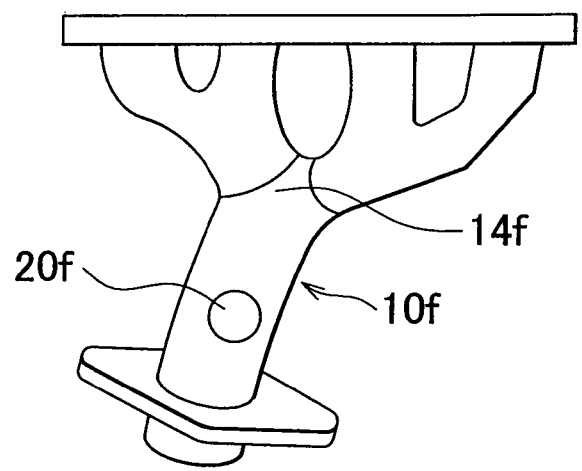
FIGS. 10A to 10C show a second example of the gas sensor fitting structure according to the third embodiment of the invention.
Figure 10B:
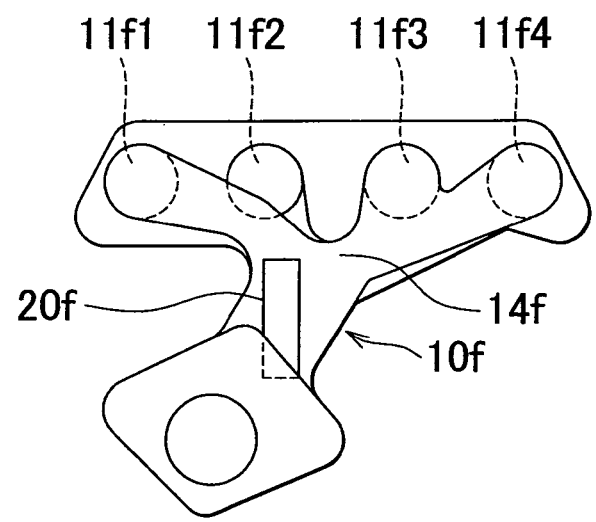
Figure 10C:
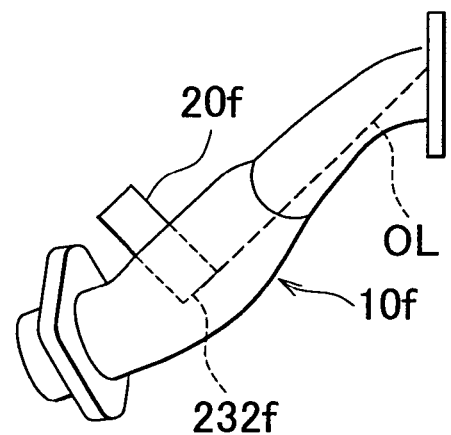

FIGS. 10A to 10C show a second example of the gas sensor fitting structure according to the third embodiment of the invention. FIG. 10A is a top view of an exhaust pipe 10f, FIG. 10B is a perspective view of the exhaust pipe 10f, and FIG. 10C is a side view of the exhaust pipe 10f. The exhaust pipe 10f includes inlet portions 11f1 to 11f4. As shown in FIG. 10A, a gas sensor 20f is fitted to the exhaust pipe 10f at a position downstream of the merging portion 14f. As shown in FIG. 10C, the gas sensor 20f is fitted to the exhaust pipe 10f in such a manner that an end face 232f is not visible from any of the inlet portions 11f1 to 11f4. Thus, it is possible to minimize occurrence of a crack in a sensor element of the gas sensor 20f due to entry of the condensed water into the gas sensor 20f.

Figure 11:
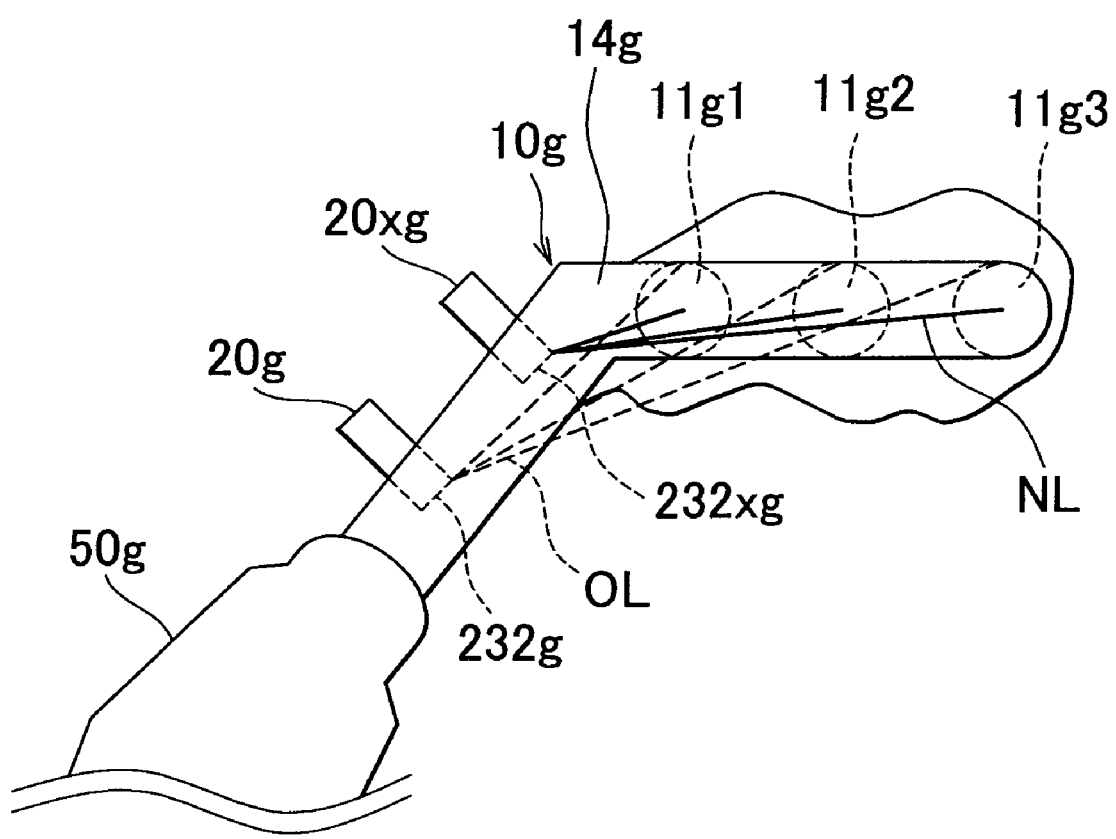
FIG. 11 shows a third example of the gas sensor fitting structure according to the third embodiment of the invention.

FIG. 11 is a third example of the gas sensor fitting structure according to the third embodiment of the invention. As shown in FIG. 11, a gas sensor 20xg is fitted to an exhaust pipe 10g at a position near a merging portion 14g, and an end face 232xg is visible from all of inlet portions 11g1 to 11g3. Therefore, there is a possibility that a crack will occur in a sensor element of the gas sensor 20xg due to entry of the condensed water into the gas sensor 20xg. In contrast, a gas sensor 20g is fitted to the exhaust pipe 10g at a position downstream of the gas sensor 20xg so that an end face 232g is not visible from any of the inlet portions 11g1 to 11g3. Therefore, it is possible to minimize occurrence of a crack in a sensor element of the gas sensor 20g due to entry of the condensed water into the gas sensor 20g. The gas sensor 20g is fitted to the exhaust pipe 10g at a position upstream of a catalyst 50g.

While the invention has been described with reference to example embodiments thereof, it is to be understood that the invention is not limited to the described embodiments or constructions. To the contrary, the invention is intended to cover various modifications and equivalent arrangements. In addition, while the various elements of the example embodiments are shown in various combinations and configurations, other combinations and configurations, including more, less or only a single element, are also within the scope of the claimed invention.

The invention claimed is:

1. A gas sensor fitting structure for fitting a gas sensor to an exhaust pipe of an internal combustion engine, comprising:
  a gas sensor including
    a sensor element, and
    a cover that covers the sensor element, the cover including
      an inner cover member having a vent-hole through an end face of the inner cover member, and
      an outer cover member disposed around the inner cover member, the outer cover member being open at an end corresponding to the end face of the inner cover member such that the end face of the inner cover member is uncovered,
  wherein the exhaust pipe has multiple inlet portions, and
  wherein the gas sensor is fitted to the exhaust pipe at a predetermined fitting angle so that the end face of the inner cover member is not visible from any position of the multiple inlet portions.

2. A gas sensor fitting structure for fitting a gas sensor to an exhaust pipe of an internal combustion engine, comprising:
  a gas sensor including
    a sensor element, and
    a cover that covers the sensor element, the cover including
      an inner cover member having a vent-hole through an end face of the inner cover member, and
      an outer cover member disposed around the inner cover member, the outer cover member being open at an end corresponding to the end face of the inner cover member such that the end face of the inner cover member is uncovered,
  wherein the exhaust pipe has a bent portion, and
  wherein the gas sensor is fitted to the exhaust pipe at a predetermined fitting angle so that the end face of the inner cover member is not visible via the bent portion from any position of an inlet portion of the exhaust pipe.

3. The gas sensor fitting structure according to claim 1, wherein the exhaust pipe has a bent portion, and
  wherein the gas sensor is fitted to the exhaust pipe at the predetermined fitting angle so that the end face of the inner cover member is not visible via the bent portion from any position of the inlet portions of the exhaust pipe.

4. The gas sensor fitting structure according to claim 1, wherein the gas sensor is fitted to the exhaust pipe at the predetermined fitting angle so that the end face of the inner cover member is not visible from any position on a virtual plane that is surrounded by one of the inlet portions.

5. The gas sensor fitting structure according to claim 4, wherein the virtual plane includes an end face of the one of the inlet portions of the exhaust pipe.

6. The gas sensor fitting structure according to claim 1, wherein the predetermined fitting angle θ satisfies the following formula:

$$\theta \leq 90° - \arctan\{(h-t)/1\},$$

where h is a diameter of the exhaust pipe, t is a distance from an inner wall face of the exhaust pipe to the end face of the inner cover member, and 1 is a distance from one of the inlet portions of the exhaust pipe to the gas sensor.

7. The gas sensor fitting structure according to claim 6, wherein the distance from the one of the inlet portions of the exhaust pipe to the gas sensor is a length of a line segment in parallel with an axis of the exhaust pipe while extending from the one of the inlet portions of the exhaust pipe to the end face of the inner cover member; and
  wherein the predetermined fitting angle of the gas sensor with respect to the exhaust pipe is an angle between the axis of the exhaust pipe and an axis of the gas sensor.

8. The gas sensor fitting structure according to claim 6, wherein the one of the inlet portions of the exhaust pipe is connected to an exhaust port of the internal combustion engine, and
  wherein the predetermined fitting angle of the gas sensor with respect to the exhaust pipe is decreased as the distance between the one of the inlet portions and the gas sensor decreases.

9. The gas sensor fitting structure according to claim 1, wherein the gas sensor is an air-fuel ratio sensor that linearly detects an air-fuel ratio based on an oxygen concentration in exhaust gas that is discharged from the internal combustion engine.

10. The gas sensor fitting structure according to claim 2, wherein the gas sensor is fitted to the exhaust pipe at the predetermined fitting angle so that the end face of the inner cover member is not visible from any position on a virtual plane that is surrounded by the inlet portion.

11. The gas sensor fitting structure according to claim 10, wherein the virtual plane includes an end face of the inlet portion of the exhaust pipe.

12. The gas sensor fitting structure according to claim 2, wherein the predetermined fitting angle θ satisfies the following formula:

$$\theta \leq 90° - \arctan\{(h-t)/1\},$$

where h is a diameter of the exhaust pipe, t is a distance from an inner wall face of the exhaust pipe to the end face of the inner cover member, and 1 is a distance from the inlet portion of the exhaust pipe to the gas sensor.

13. The gas sensor fitting structure according to claim 12, wherein the distance from the inlet portion of the exhaust pipe to the gas sensor is a length of a line segment in parallel with an axis of the exhaust pipe while extending from the inlet portion of the exhaust pipe to the end face of the inner cover member; and wherein the predetermined fitting angle of the gas sensor with respect to the exhaust pipe is an angle between the axis of the exhaust pipe and an axis of the gas sensor.

14. The gas sensor fitting structure according to claim 12, wherein the inlet portion of the exhaust pipe is connected to an exhaust port of the internal combustion engine, and the predetermined fitting angle of the gas sensor with respect to the exhaust pipe is decreased as the distance between the inlet portion and the gas sensor decreases.

15. The gas sensor fitting structure according to claim 2, wherein the gas sensor is an air-fuel ratio sensor that linearly detects an air-fuel ratio based on an oxygen concentration in exhaust gas that is discharged from the internal combustion engine.

16. An apparatus, comprising:

an exhaust pipe including an inlet portion; and a gas sensor disposed through a wall of the exhaust pipe at a predetermined fitting angle such that an axis of the gas sensor is inclined with respect to an axis of the exhaust pipe, the gas sensor including a sensor element, a tubular inner cover having a closed end face and a vent-hole through the closed end face, an area of the vent-hole being less than an area of the closed end face, and a tubular outer cover that surrounds longitudinal sides of the inner cover, an end of the outer cover, which corresponds to the end face of the inner cover member such that the closed end face of the inner cover member is directly exposed to an interior of the exhaust pipe, wherein the gas sensor is inclined in the exhaust pipe such that a straight line from any position of the inlet portion does not intersect the closed end face of the inner cover unless the straight line first intersects the outer cover.

* * * * *